United States Patent [19]

Lewis et al.

[11] 4,216,315

[45] Aug. 5, 1980

[54] PROCESS FOR PURIFICATION AND RECOVERY OF CYANURIC ACID

[75] Inventors: Harvie H. Lewis, Mechanicsville, Va.; Neal E. Morganson, Pittsburgh, Pa.; Raymond J. Smialek, Lake Charles, La.

[73] Assignee: Olin Corporation, New Haven, Conn.

[21] Appl. No.: 35,881

[22] Filed: May 4, 1979

[51] Int. Cl.$^2$ .......................................... C07D 251/32
[52] U.S. Cl. .................................................... 544/192
[58] Field of Search ........................................ 544/192

[56] References Cited

U.S. PATENT DOCUMENTS

| | | | |
|---|---|---|---|
| 2,712,002 | 6/1955 | Lundberg | 260/248 A |
| 3,107,244 | 10/1963 | Robertson | 260/248 A |
| 3,994,892 | 11/1976 | DenOtter et al. | 260/248 A |

*Primary Examiner*—John M. Ford
*Attorney, Agent, or Firm*—James B. Haglind; Donald F. Clements

[57] ABSTRACT

A process is described for the purification and recovery of cyanuric acid from a hot slurry of cyanuric acid in an organic solvent. In the process, the hot slurry is quenched in a quench liquid which is at a temperature for cooling the hot slurry to form a cooled slurry of cyanuric acid particles in a mixture of the solvent and the quench liquid. Cyanuric acid particles are separated from the mixture of solvent and quench liquid and recovered.

The process effectively cools and separates cyanuric acid from the solvent and any color bodies present to produce a pure white crystalline product.

23 Claims, No Drawings

PROCESS FOR PURIFICATION AND RECOVERY OF CYANURIC ACID

This invention relates to the production of cyanuric acid. More particularly, this invention relates to the purification and recovery of cyanuric acid from reaction slurries containing a polar solvent.

Cyanuric acid can be produced by heating urea or biuret in a solvent medium. During the process, particles of cyanuric acid are formed as a slurry in the hot solvent. Previous processes have employed operations to cool the reaction slurry and to separate the cyanuric acid from the slurry in which cyanuric acid was deposited on the cooling surfaces and the resulting product was discolored.

A process is therefore required for producing cyanuric acid in a solvent medium which eliminates the deposition of product on cooling surfaces and which produces a white cyanuric acid product.

It is therefore an object of the present invention to provide a process having improved purification and recovery procedures for cyanuric acid.

Another object of the present invention is to provide a process having an improved cooling procedure for cyanuric acid slurries in a solvent medium.

A further object of the present invention is to provide a process for the production of cyanuric acid which can employ concentrated slurries of cyanuric acid in a solvent medium.

An additional object of the present invention is to provide a process to produce a cyanuric acid product free of discoloration.

These and other objects of the invention are accomplished in a process for the purification and recovery of cyanuric acid from a hot slurry of the cyanuric acid in an organic solvent which comprises:

(a) quenching the hot slurry in a quench liquid to form a first cooled slurry of cyanuric acid particles in a mixture of the solvent and the quench liquid, the quench liquid being at a temperature suitable for cooling the first hot slurry, (b) separating the cyanuric acid particles from the mixture of solvent and quench liquid, and (c) recovering said cyanuric acid particles.

In the pyrolysis process, urea is fed to a body of an organic solvent at temperatures up to about the boiling point of the solvent, for example, in the range of about 150° to about 300° C. During the pyrolysis process, the urea is converted to cyanuric acid and a slurry of cyanuric acid in the hot solvent is produced. The slurry contains from about 20 to about 70, preferably from about 25 to about 65, and more preferably from about 40 to about 65 percent by weight of cyanuric acid.

Suitable solvents in which the pyrolysis reaction may be conducted include, for example, alkyl cyclohexanols, methoxy ethoxy isopropanols, tetrahydrofurfuryl alcohol, alkyl sulfones, dialkyl sulfones, dialkyl ethers of polyalkylene glycols, alkyl pyrrolidones, cycloalkyl pyrrolidones, diphenyl oxide, and alkyl oxazolidinones.

Processes for the pyrolysis of urea in these solvents are described, for example, in U.S. Pat. No. 3,008,961, issued Nov. 14, 1961, to B. H. Wojcik; U.S. Pat. No. 3,065,233, issued Nov. 20, 1962, to T. R. Hopkins et al; U.S. Pat. No. 3,117,968, issued Jan. 14, 1964, to K. Merkel et al; U.S. Pat. No. 3,164,591, issued Jan. 5, 1965, to W. E. Walles et al; U.S. Pat. No. 3,563,987, issued Feb. 16, 1971, to S. Berkowitz; U.S. Pat. No. 3,635,968, issued Jan. 18, 1962, to H. Goelz et al; U.S. Pat. No. 3,810,891, issued May 14, 1974, to J. M. Lee as well as Canadian Pat. No. 687,279, issued May 26, 1964, to B. H. Wojcik; Canadian Pat. No. 729,190, issued Mar. 1, 1966, to R. M. Thomas; and Canadian Pat. No. 740,444, issued Aug. 9, 1966, to R. E. Bailey et al.

During the pyrolysis, some decomposition of the solvent can occur, causing the formation of color bodies which contaminate the product. In the novel process of the present invention, those color bodies are separated by quenching the hot slurry in a quench liquid. The quench liquid may be any liquid which facilitates the separation of cyanuric acid from the solvent used in the pyrolysis process. Suitable quench liquids include, for example, water, alcohols such as methanol, ethanol, and isopropanol, glycols such as ethylene glycol and diethylene glycol as well as aqueous solutions of alcohols and glycols. Preferred as the quench liquid is an aqueous liquid such as water, a mixture of water and the pyrolysis solvent, an aqueous solution of the pyrolysis solvent, or an aqueous solution containing low concentrations of cyanuric acid. The quench liquid is charged to a closed reaction vessel at a temperature sufficiently below that of the hot slurry to cool the hot slurry of cyanuric acid in the solvent. Suitable temperatures are those below the boiling point of the quench liquid. Preferably the temperature of the quench liquid at atmospheric pressure, is in the range of from about 0° to about 90° C., and more preferably at from about 10° to about 50° C.

In the process of the present invention, the hot slurry of cyanuric acid in the solvent is discharged from the pyrolysis reactor to the quench liquid. Any suitable method may be used to charge the hot slurry to the quench liquid. For example, the hot slurry may flow by gravity means into the quench liquid or the hot slurry may be sprayed into the quench liquid. The rate of charging the hot slurry to the quench liquid is not critical, but preferably the hot slurry is fed to the quench liquid at a rate which effectively cools the hot slurry while preventing localized boiling of the quench liquid. Where the hot slurry is gravity fed to the quench liquid, the flow may be controlled, for example, by choking or throttling the slurry. Upon contacting the quench liquid, the cyanuric acid particles are rapidly cooled.

The quench liquid is agitated to effectively disperse the hot slurry into the quench liquid and separate cyanuric acid particles from the solvent employed. Color bodies present in the hot slurry are taken up by the mixture of quench liquid and solvent.

Where a non-aqueous liquid is used as the quench liquid, the hot slurry may be cooled to any desired temperature before separating the cyanuric acid from the mixture of quench liquid and solvent.

When water or an aqueous solution is used as the quench liquid, it should be noted that cyanuric acid forms a hydrate at a temperature of about 52° C. at atmospheric pressure. However, this temperature will vary with pressure and may be lower at reduced pressures. Crystals of hydrated cyanuric acid, if allowed to form on a separating device such as a filter or centrifuge, can harden on the separator into a cake of cement-like mass. Formation of hydrate crystals on the separator clogs these devices so that separation times are increased, and the crystals are difficult if not impossible to remove without damaging the filter or centrifuge screens.

In one embodiment of the process of the present invention where water is present in the quench liquid, the quench liquid is at temperatures which cool the hot slurry, but prevent the formation of cyanuric acid hydrate. Cyanuric acid particles are effectively separated from the solvent and any color bodies present are separated, dispersed, or dissolved. The anhydrous cyanuric acid crystals obtained during the quenching are at a temperature above about 52° C. at atmospheric pressure, and are separated from the mixture of quench liquid and solvent in a separating device and washed under conditions which prevent the formation of hydrated cyanuric acid.

In another embodiment, the hot slurry is cooled in a quench liquid containing water to a temperature below about 52° C., and preferably below about 50° C. At these lower temperatures, crystals of hydrated cyanuric acid form in the quench liquid. The preforming of hydrated cyanuric acid crystals permits their separation in devices such as filters or centrifuges without the formation in these vessels of hydrated cyanuric acid deposits. Deposits of hydrated cyanuric acid formed in these devices results in clogging these devices and reducing product filterability, product yields, etc. In addition, cooling the cyanuric acid to a temperature below about 50° C. reduces the amount of cyanuric acid which will be dissolved by the quench liquid and solvent mixture.

To assure that crystals of a cyanuric acid hydrate such as the dihydrate are formed in this embodiment, the cyanuric acid particles are kept in the quench liquid a suitable period of time. While this time period will vary with, for example, the temperature of the quenched slurry, a suitable time is from about 5 to about 500 minutes, preferably from about 10 to about 200 minutes, and more preferably from about 15 to about 100 minutes.

Any suitable amount of quench liquid may be employed to cool the hot slurry to the desired temperature range. However, to efficiently cool the hot slurry while minimizing the cost of solvent recovery, the cooling is preferably effected in two stages. In this embodiment, the hot slurry is charged into the quench liquid for initial cooling. The initially cooled slurry is then further cooled using, for example, external cooling means or evaporative cooling. For example, where the quench liquid contains water, the hot slurry of cyanuric acid is initially cooled by the quench liquid to a temperature above about 52° C. The slurry of cyanuric acid in the mixture of solvent and quench liquid is then, for example, evaporatively cooled to temperatures below about 52° C. to produce hydrated cyanuric acid.

Where two stage cooling is employed, suitable amounts of quench liquid include those having a weight ratio of quench liquid to hot slurry of from about 0.2:1 to about 4:1 and preferably from about 0.4:1 to about 2.5:1.

While it is preferred that initially quenching be done at atmospheric pressure, higher or lower pressures may be employed, if desired.

During quenching, it is desirable to agitate the quench liquid to improve contact between the cyanuric acid particles and the quench liquid for both cooling and solvent separation purposes.

Following quenching, the cyanuric acid crystals may be separated from the mother liquor comprised of the mixture of solvent and quench liquid by employing a separator such as a centrifuge or filter. As stated above, the hydrated cyanuric acid is preferably formed before separation at a temperature below about 52° C. This permits the separation of the solid hydrated cyanuric acid from the liquid mixture with a minimum of clogging or plugging of the separator openings. After separation of cyanuric acid crystals, all or a portion of this mother liquor may be recycled to the quenching operation to be used as quench liquid. The solvent may be recovered from this mother liquor, for example, by distillation which also removes color bodies present.

To remove any entrapped solvent from the separated cyanuric acid crystals, they are washed with, for example, water. Wash water containing minor amounts of solvent and traces of cyanuric acid can be recycled for use as a portion or all of the quench liquid.

Cyanuric acid crystals produced by the novel process of the present invention are essentially solvent-free, assay in excess of 99 percent cyanuric acid, and are free from color bodies. The white crystalline product can be employed without further treatment in the production of compounds such as chloroisocyanuric acids as well as in the stabilization of these and other available chlorine-containing materials which are used in the treatment of swimming pool water.

When the hot slurry is cooled by the quenching process of the present invention, additional benefits result in that the solvent is cooled under conditions which minimize the possible oxidation of the solvent upon contacting air. Further, the quenching process effectively separates the cyanuric acid particles from the solvent and allows for the recovery of substantially solvent-free cyanuric acid.

The novel process of the present invention is further illustrated by the following examples.

EXAMPLE 1

Molten urea was fed to a reaction vessel containing N-cyclohexyl pyrrolidone as the solvent and pyrolyzed to produce a hot slurry containing cyanuric acid crystals. When sufficient urea had been reacted to provide a weight of cyanuric acid in the slurry of about 41 percent, the hot tan-colored slurry, at a temperature of about 210° C., was throttled into a quench tank. The quench tank, a vented closed vessel equipped with an agitator and cooling jacket, contained water at a temperature of about 25° C., the weight ratio of water to hot slurry charged being about 1.4:1. As the hot slurry contacted the quench liquid, the slurry was cooled rapidly to a temperature below 100° C. Rapid cooling of the hot slurry inhibited oxidation of the solvent. Circulation of cold water through the cooling jacket further lowered the temperature of the cyanuric acid slurry to about 40° C. The slurry was held at this temperature for 30 minutes to permit cyanuric acid hydrate crystals to form. The quenched slurry containing cool hydrated cyanuric acid crystals in a mixture of water and N-cyclohexylpyrrolidone was fed to a centrifuge. A cake of hydrated cyanuric acid was separated from a mother liquor composed of a mixture of water and solvent and about one-half of the mother liquor was returned to the quench tank. Remaining mother liquor was fed to a distillation column to recover the solvent and remove color bodies. Water at a temperature of 25° C. was fed to the centrifuge to wash the cake and remove any adhering solvent and color bodies present. After additional centrifuging to remove wash water, the white cyanuric acid cake was removed from the centrifuge. Anhydrous cyanuric acid was obtained by heating the cake in an oven at 110° C. The product had an assay of 99.2 percent by weight of cyanuric acid.

EXAMPLE 2

The procedure of EXAMPLE 1 was repeated with the exception that prior to quenching, the reaction slurry was held in the reactor for about 2 hours after the reaction had been completed and cooled to a temperature of 195° C. The hot slurry was quenched in a quench liquid comprised of water and mother liquor (a mixture of water and solvent from a previous quench operation). Product separation and recovery procedures were the same as those used in EXAMPLE 1.

EXAMPLE 3

The procedure of EXAMPLE 1 was repeated with the exception that following completion of the pyrolysis reaction, the temperature of the cyanuric acid slurry was 228° C. before being quenched.

EXAMPLE 4

The procedure of EXAMPLE 1 was repeated with the exception that the quench liquid was comprised of water where the weight ratio of water to hot slurry was about 1.0:1.0.

EXAMPLE 5

The procedure of EXAMPLE 1 was repeated with the exception that the weight ratio of water used as the quench liquid to hot slurry was about 3.0:1.0.

EXAMPLE 6

A hot slurry containing 40 percent by weight of cyanuric acid was prepared by the procedure of EXAMPLE 1. The hot slurry was cooled to 90° C. then quenched in deionized water. This produced a quenched slurry at a temperature of 59° C. The cooled slurry was removed quickly from the quench liquid and fed to a steam heated filter which maintained the temperature of the cyanuric acid above 52° C. during filtering. The heated filter cake was washed with hot water and removed without difficulty from the filter. The cake was oven dried to produce white anhydrous crystals of cyanuric acid.

EXAMPLE 7

A hot slurry containing 42.5 precent by weight of cyanuric acid was produced by the procedure of EXAMPLE 1. The slurry, at 220° C., was fed to a quench tank containing water and mother liquor from a previous quench which initially cooled the hot slurry to 65° C. Cold water circulating through a jacket on the quench tank further cooled the slurry from 65° to 52° C. in 19 minutes. Circulation of the cooling water was stopped. The slurry was held in the quench tank for an additional ten minutes during which its temperature dropped from 52° to 48° C. After product separation and washing, the white crystals were analyzed and found to be hydrated cyanuric acid containing 24.5 percent by weight of water.

EXAMPLE 8

A cool quenched slurry of hydrated cyanuric acid (42° C.) was fed to a centrifuge and separated from mother liquor. Prior to washing, a sample of the cake was analyzed and found to contain concentrations of adhering solvent, N-cyclohexylpyrrolidone, in the range of 2.5 to 5 percent by weight. The cake was washed by spraying water on the face of the spinning centrifuge cake. Analysis of the washed cake found the solvent concentration had been reduced to 0.17 percent by weight.

What is claimed is:

1. A process for the purification and recovery of cyanuric acid from a hot slurry of said cyanuric acid in an organic solvent which comprises:
   (a) quenching said hot slurry in a quench liquid to form a first cooled slurry of cyanuric acid particles in a mixture of said solvent and said quench liquid, said quench liquid being at a temperature suitable for cooling said hot slurry,
   (b) separating said cyanuric acid particles from said mixture of said solvent and said quench liquid, and
   (c) recovering said cyanuric acid particles.

2. The process of claim 1 in which the temperature of said hot slurry is from about 150° to about 300° C.

3. The process of claim 2 in which said hot slurry of said cyanuric acid contains from about 20 to about 70 percent by weight of cyanuric acid.

4. The process of claim 3 in which said quench liquid is at a temperature of from about 0° to about 90° C.

5. The process of claim 4 in which said quench liquid is an aqueous liquid.

6. The process of claim 5 in which said temperature of said first cooled slurry is maintained at a temperature above the temperature of hydration of said cyanuric acid.

7. The process of claim 4 in which additional cooling is applied to said first cooled slurry to form a second cooled slurry.

8. The process of claim 7 in which the weight ratio of said quench liquid to said hot slurry is from about 0.2:1 to about 4:1.

9. The process of claim 8 in which the temperature of said quench liquid is from about 10° to about 50° C.

10. The process of claim 9 in which said second cooled slurry is formed by the evaporative cooling of said first cooled slurry.

11. The process of claim 10 in which said temperature of said second cooled slurry is below the temperature of hydration of said cyanuric acid.

12. The process of claim 11 in which said weight ratio of said quench liquid to said hot slurry is from about 0.4:1 to about 2.5:1.

13. The process of claim 12 in which said second cooled slurry is held for a period of from about 5 to 500 minutes for hydrated cyanuric acid to form.

14. The process of claim 13 in which said quench liquid is water.

15. The process of claim 13 in which said quench liquid is a mixture of water and said solvent.

16. A process for the production of cyanuric acid by the pyrolysis of urea in a solvent which comprises:
   (a) pyrolyzing said urea at a temperature in the range of from about 150° to about 300° C. to form a hot slurry of cyanuric acid in said solvent,
   (b) quenching said hot slurry in a quench liquid to form a cooled slurry of cyanuric acid particles in a mixture of said solvent and said quench liquid, said quench liquid being an aqueous liquid at a temperature suitable for cooling said hot slurry,
   (c) further cooling said cooled slurry to a temperature below the temperature of hydration of said cyanuric acid to form a hydrated cyanuric acid slurry,
   (d) separating said hydrated cyanuric acid from said mixture of said solvent and said quench liquid, and
   (e) recovering said hydrated cyanuric acid.

17. The process of claim 16 in which said hot slurry has a concentration of cyanuric acid of from about 25 to about 65 percent by weight of said cyanuric acid.

18. The process of claim 17 in which said quench liquid is at a temperature of from about 0° to about 90° C.

19. The process of claim 18 in which the weight ratio of said quench liquid to said hot slurry is from about 0.2:1 to about 4:1.

20. The process of claim 19 in which said cooling in step (c) comprises evaporative cooling of said second cooled slurry.

21. The process of claim 20 in which said separating of said hydrated cyanuric acid particles from said mixture of said solvent and said quench liquid is accomplished in a centrifuge.

22. The process of claim 21 in which said hydrated cyanuric acid particles are washed with water, a portion of said wash water being recovered for use as quench liquid.

23. The process of claim 22 in which the temperature of said quench liquid is from about 10° to about 50° C. and the weight ratio of said quench liquid to said hot slurry is from about b 0.4:1 to about 2.5:1.

* * * * *